United States Patent [19]

Paluch

[11] 3,945,378

[45]*Mar. 23, 1976

[54] POSITIVE PRESSURE BREATHING CIRCUIT

[76] Inventor: Bernard R. Paluch, 1607 E. Cedar Lane, Mount Prospect, Ill. 60056

[ * ] Notice: The portion of the term of this patent subsequent to Feb. 11, 1992, has been disclaimed.

[22] Filed: Feb. 10, 1975

[21] Appl. No.: 548,367

Related U.S. Application Data

[63] Continuation-in-part of Ser. No. 451,855, March 18, 1974, Pat. No. 3,865,106.

[52] U.S. Cl. ............................ 128/145.8; 128/188
[51] Int. Cl.² ......................................... A61M 17/00
[58] Field of Search ........... 128/145.8, 146.5, 146.4, 128/145.5, 142.2, 142.3, 191 R, 188, 187, 186, 193, 194, 351 R, 351 BV; 251/5; 138/93 R; 261/116, 120, DIG. 65

[56] References Cited
UNITED STATES PATENTS

| | | | |
|---|---|---|---|
| 1,510,212 | 9/1924 | Du Bois | 138/93 |
| 3,504,676 | 4/1970 | Lomholt | 128/351 |
| 3,814,091 | 6/1974 | Henkin | 128/145.8 |

FOREIGN PATENTS OR APPLICATIONS

| | | | |
|---|---|---|---|
| 520,342 | 7/1920 | France | 128/191 R |

*Primary Examiner*—Robert W. Michell
*Assistant Examiner*—Henry J. Recla
*Attorney, Agent, or Firm*—Dominik, Knechtel, Godula & Demeur

[57] ABSTRACT

A positive pressure breathing circuit for operation in conjunction with a positive pressure ventilator including a concentrically oriented inhalation/exhalation circuit having an inner inhalation tube and an outer exhalation tube, the tubes being positioned in concentric and spaced orientation, the inhalation tube being further provided with an inhalation unidirectional valve means for providing unidirectional gas flow through the inhalation tube, the exhalation tube being provided with an exhalation unidirectional valve means associated therewith for providing unidirectional gas flow through the exhalation tube, and an inflatable occlusion means interposed between the inner and outer tubes in fluid communication with a source of pressurized fluid, such that the inflatable occlusion means is alternatively inflatable and deflatable in response to fluid pressure from the source thereof, the gas flow in the inhalation tube being countercurrent with respect to the gas flow in the exhalation tube, and the circuit further being provided with disengagably mountable nebulizer means in cartridge form and in fluid communication with the inhalation tube, such that atomized medicinal fluids may be introduced into the inhalation tube during the respiratory therapy.

9 Claims, 15 Drawing Figures

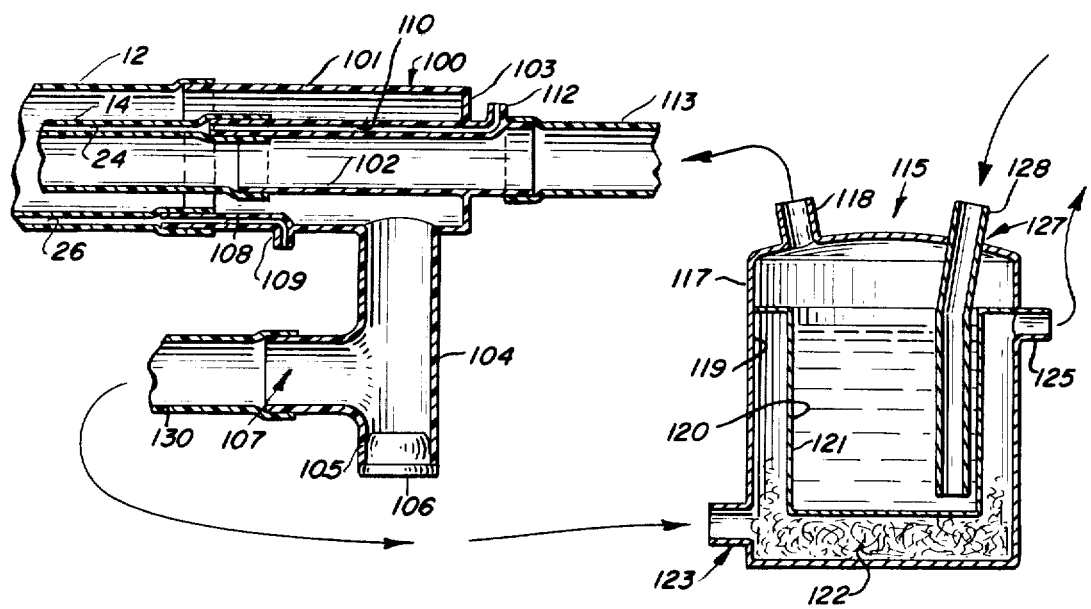
FIG. 10
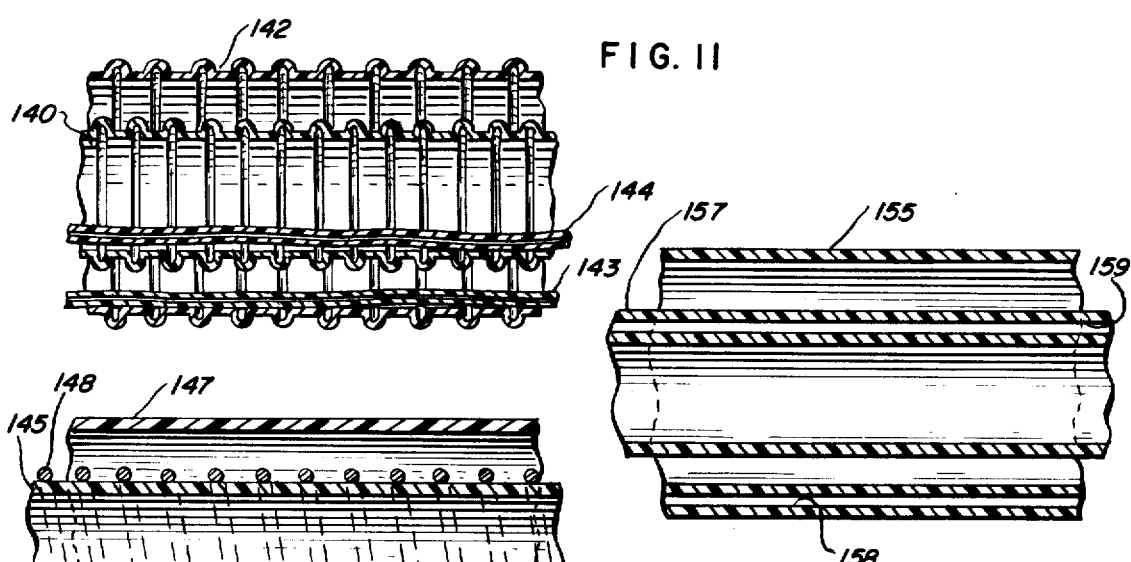
FIG. 11
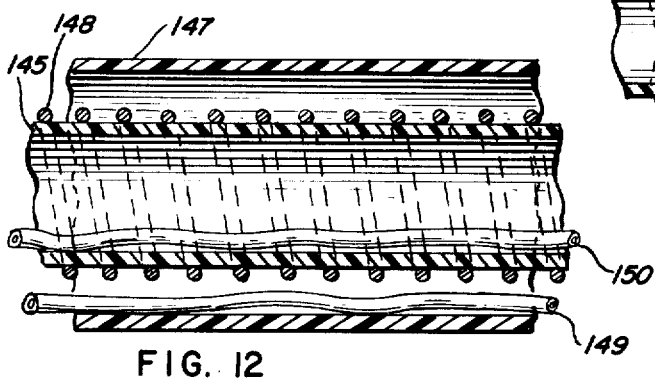
FIG. 12
FIG. 13

POSITIVE PRESSURE BREATHING CIRCUIT

CROSS REFERENCE TO RELATED APPLICATIONS

This application is a continuation-in-part of co-pending application Ser. No. 451,855 filed in the name of Bernard R. Paluch, and entitled Positive Pressure Breathing Circuit, filed on March 18, 1974, now U.S. Pat. No. 3,865,106, issued on Feb. 11, 1975.

BACKGROUND OF THE INVENTION

The concept of respiratory therapy is well known in the art field, and a wide variety of respiratory diseases are treated by use of a positive pressure respiratory system. The positive pressure incident to such systems is generated by devices commonly referred to as ventilators, respirators or other such positive pressure machines. Generally, the concept is to provide a breathable gas mixture under pressure to the patient to facilitate the respiratory cycle of the patient.

Usually, such breathable gases consist of a composition of air and oxygen which is delivered to the patient under controlled conditions of pressure, temperature, water content and gas composition.

In the typical system, the gas is conducted from the ventilator to the patient by means of a tubing conduit, generally consisting of an inhalation tube and exhaled gases exhausted through an exhalation tube. Furthermore, it is generally accepted that in such systems, the inhalation and exhalation tubes respectively, are separate tubes separately interconnecting the ventilator with the patient face mask in order to complete the circuit as between the ventilator and the patient. The differences existing between the variety of systems available generally involve mainly materials of construction rather than in the make-up of the system. The tubing conduit is usually formed of a flexible material, which is chemically inert and fabricated into a cylindrical configuration, whether corrugated or otherwise, and reinforced in order to prevent kinking and collapse. The tubes or conduits are interconnected to the ventilator and to the patient by any suitable devices, although usually slip-type friction fittings are employed especially for connection of the ventilator to the valving mechanism which is external to the patient. In addition, many of the current respiratory breathing circuits also incorporate a gas powered nebulizer, usually mounted to the housing of the valving mechanism, the nebulizer functioning to create a mist of a variety of liquid medications, which are then administered in conjunction with the positive gas pressure introduced through the inhalation tube.

Another feature of a respiratory circuit and system includes the provision of a heated humidifier which is interposed in the circuit between the ventilator and the inhalation tube. The purpose of the heated humidifier is to raise the temperature of the gas as well as to humidify the same prior to inhalation by the patient. In the usual system, the heater raises the liquid temperature to approximately 120°–140° F. which results in a gas temperature of approximately 110°–130° F. upon exit from the nebulizer or humidifer.

Insofar as the presently existing systems are concerned, a variety of problems have been encountered and it is the purpose of the present invention to overcome these difficulties which are inherent in the present systems. For example, the valving mechanism incident to systems presently available are generally extraneous to the system and the circuit, and hence, a great deal of dead space is usually present in the system. The dead space results in the patient generally breathing in previously exhaled gases during the inhalation cycle since any gas existing in the dead space will tend to be drawn back into the patient during the inhalation cycle. In the event that any bacterial growth develops in the dead space, it is obvious that the patient is exposed to the danger of inhaling contaminated gas.

In addition, $CO_2$ is a respiratory stimulant and can cause hyper-ventilation with attendant unfavorable complications. Hence, it is deemed desirable not only to have the valving mechanism associated with the circuit per se, but also to position the valving mechanism closely adjacent to the patient to minimize the dead space.

Insofar as humidification and heating is concerned, it has been found that since the humidifier is generally positioned in the circuit in a position removed from the patient, that even though the gas may be heated and humidified, the gas will give off both heat and humidity as it travels through the tubing to the patient. For example, when the heat-saturated gas leaves the humidifier through the tubing circuit, it will release heat by contact with the thin wall of the tubing conduit, which in turn is exposed to room air temperature, i.e. 70°–75' F. Hence, it is frequently found that the inlet gas temperature just prior to entering the patient is approximately 85° F. thereby accounting for a temperature drop of approximately 25° F or more. As a result of the heat given up by the gas, condensation will occur in the tubing circuit resulting in a pool of liquid collecting in the tubing. It is apparent that the pooling of liquid in the tubing circuit is not desirable since such pooling actually reduces the lumen opening of the tubing at the point of pooling, which in turn may cause premature cycling of a pressure-cycled ventilator, since the reduced lumen presents a pressure gradient which the ventilator senses as a pressure increase. If the pressure equals the shut-off pressure of the ventilator, the ventilator will cycle off and the patient will not have received the proper pressure from the ventilator system. In a volume-cycled ventilator, the reduction in lumen at the point of pooling reduces the volume of gas delivered to the patient since the gas between the ventilator and the pool is compressed and hence, the patient does not receive the proper volume of gas. Furthermore, the compression of the gas is reflected in tubing compliance, or the distention of the tubing as a result of internal pressure and is an important factor in determining the setting of volume-cycled ventilators and is generally compensated for in making the initial settings of the ventilators. The change in volume produced by pooling, however, is not predictable and consequently, cannot be compensated for in the ventilator setting. In presently existing systems, this situation is compensated for by draining the tubing at frequent intervals in order to relieve the pooling problems. It is hence deemed desirable to reduce the amount of condensation in the tubing and one of the purposes of the present invention is to greatly reduce this problem.

Another problem incident to the heat loss of the gases as they travel through the tubing conduit from the humidifier to the patient is that if the temperature of the inhaled gas is below body temperature, there is a tendency of the body of the patient to give up heat to the gas. The heat given up by the patient is energy released as a result of the work by the patient's metabolic system and the continued demand for heat release requires the metabolic system to work harder and this work can become a significant factor in treating a critically ill patient. Additionally, as the temperature of the inhaled gas is raised, through heat loss by the patient, its relative humidity decreases. A humidity deficit in the gas is then created and since the gas can carry additional moisture as water vapor, the tendency is for the mucosal membranes in the respiratory system of the patient's body to give up water until the inhaled gas is saturated. This surrender of water vapor from the patient's mucosal membranes can cause complications since the mucous on those membranes will become drier and more viscous, making it more difficult to remove by cillial action. The accumulation of mucous inhibits adequate ventilation and can cause alveolar collapse infection, changes in blood gas levels, and other complications of a serious nature.

The present systems have attempted to alleviate this problem by increasing the moisture and temperature of the gas upon leaving the humidifier. However, it is apparent that where the gas is heated above body temperature in order to ensure a temperature close to body temperature upon delivery to the patient, the gas will pick up additional quantities of moisture in the humidifier and will lose the same through "rain out" during its travel through the tubing conduit. Hence, more frequent draining of the tubing conduit has been necessary where humidification is employed.

It is therefore deemed desirable to minimize the amount of extra heat generated in the humidifier while at the same time preventing and retarding heat loss in the tubing conduit since one is thereby more assured of the proper humidity and temperature level of the gas upon inhalation by the patient. It is another feature of this invention to provide a system which accomplishes this end.

Another difficulty which has been inherent in presently available systems relates to the nebulizer utilized to introduce atomized medications into the inhalation line. Present systems generally require that an operator manually fill the nebulizer prior to the respiratory therapy for the patient, and this operation is both time consuming and subject to human error. Furthermore, additional problems with sterility are introduced when an operator handles the nebulizer, especially where the nebulizer is intended to be in fluid communication with the tubing circuit for delivery of medicinal fluids to the patient. While the present nebulizers are relatively effective in creating atomization of the medicinal liquids therein, such nebulizers are affected in different degrees by the position of the nebulizer assembly with respect to the vertical-horizontal axis. For example, if the bottom of the capillary tube within the nebulizer is improperly positioned within the housing, no liquid will be aspirated in the capillary tubing. The present invention overcomes this difficulty by providing an improved and more simplified nebulizer including a capillary tube system which is designed to flotate on the surface of the medicinal fluid contained in the nebulizer and ensure that atomization of the medicinal fluid therein will occur during the inhalation therapy.

OBJECTS AND ADVANTAGES

It is therefore the principal object of the invention described herein to provide a positive pressure breathing circuit which is compact in structure while at the same time minimizes heat loss of the gas during travel through the tubing circuit while maintaining a relatively stable level of humidification of the gas prior to inhalation by the patient.

In connection with the foregoing object, it is yet a further object of this invention to provide a system which retains the heat of the inhaled gas throughout the path of travel through the tubing circuit without at the same time employing any extraneous heat source, this goal being accomlished by providing a heat exchanger system utilizing both the inhaled gases as well as the exhaled gases to provide such a heat exchanger system.

Still another object of the invention is to provide a positive pressure breathing circuit which includes both inhalation and exhalation unidirectional valve means, thereby to ensure unidirectional gas flow through the inhalation line, as well as through the exhalation line, and thereby preventing any cross-contamination of the gases in the circuit.

In connection with the foregoing object, it is another object to provide a positive pressure breathing circuit of the type described which also includes inflatable occlusion means in fluid communication with a source of pressurized fluid which is designed to inflate during the inhalation cycle thereby to occlude the space between the inhalation tube and the exhalation tube and function as a resistance to any back pressure created as well as to absolutely prevent any cross contamination of exhaled gases with inhaled gases during both the inhalation and exhalation cycles of the patient.

Yet a further object of the invention is to provide an improved positive pressure breathing circuit which is provided with a disengagably mountable nebulizer cartridge which may be prefilled under sterile conditions and easily mounted on the tubing circuit, thereby to establish fluid communication as between the nebulizer and the inhalation tube while at the same time minimizing handling by the operator, as well as simplifying installation of the nebulizer to the circuit.

In connection with the foregoing object it is yet another object of the invention to provide an improved nebulizer wherein the capillary tube system has been improved such that the capillary tube causing the atomization of the medicinal fluids therein is designed to float on the surface of the liquid level within the nebulizer and thereby ensure complete atomization of the medicinal fluids contained therein and minimize improper positioning of the capillary tube system therein.

A further object of the invention is to provide a positive pressure breathing circuit wherein the inhalation tube and exhalation tube are positioned in concentric double tubular orientation, with the inhalation line being positioned interiorly of the exhalation line such as to create a heat exchanger system whereby the heat of the exhaled gases will simultaneously warm the inhaled gases and retard heat loss of the inhaled gas throughout the course of travel through the system, thereby ensuring that the inhaled gases will maintain both heat and humidity until inhaled by the patient, while at the same time providing a system which is compact in construction and efficient in operation, and also incorporating the valving mechanisms for both the inhalation tube and exhalation tube within the tubing circuit and immediately adjacent to the patient, and further permitting the inflatable occlusion means to be positioned within the tubing circuit, again adjacent to the patient receiving terminal end thereof.

In connection with the foregoing object, it is yet a further object to provide a positive pressure breathing circuit of the type described wherein the nebulizer means may be easily positioned and mounted onto the exhalation tube and readily establish fluid communication between the nebulizer means and the inhalation tube, while at the same time avoiding the possibility of interfering with the sterile condition of the nebulizer or its contents.

Still another feature of the present invention is the provision of an improved humidifer which is provided with an outer jacket surrounding the water chamber and constructed to be in fluid communication with the exhaled gases at the terminal end of the exhalation tube, such that the heat from the exhaled gases may be used to maintain the temperature of the water within the humidifer hence permitting the utilization of the gases within the system, thereby to permit the greatest amount of energy conservation.

Further features of the invention pertain to the particular arrangement of the elements and parts whereby the above outlined and additional operating features thereof are attained.

The invention both as to its organization and method of operation, together with further objects and advantages thereof, will best be understood by reference to the following specification, taken in connection with the accompanying drawings in which:

FIG. 10 is a side elevational cross-sectional view showing the gas source end of the circuit and the interconnection thereof with the humidifier for the system;

FIG. 11 is a side elevational cross-sectional view showing one embodiment of the tubing useful in the present invention;

FIG. 12 is a side elevational cross-sectional view showing a smooth walled tubing configuration useful within the purview of the present invention, wherein the interior tube includes a helical wire wound thereabout;

FIG. 13 is a side elevational cross-sectional view showing an embodiment of the invention wherein smooth walled tubing is utilized.

Figure 1:
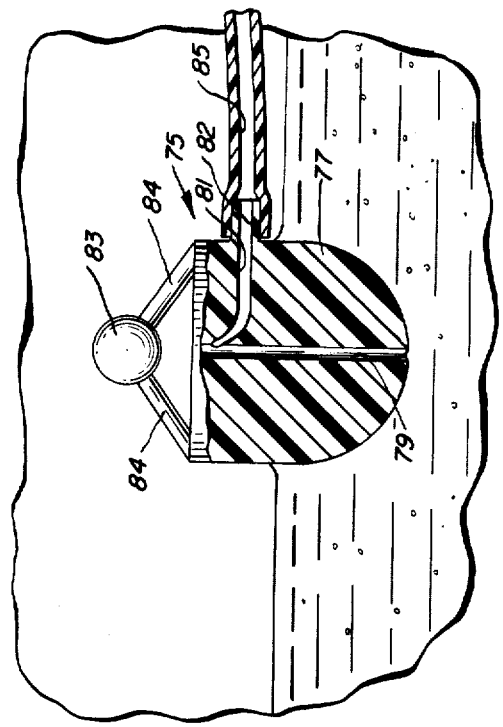
FIG. 1 is a side elevational cross sectional view of the positive pressure breathing system, showing the double tubular concentric orientation of the inhalation and exhalation lines and the valving system for the circuit, including the inflatable occlusion means and the novel nebulizer means for the invention.

With specific reference to FIG. 1 of the drawings, the details of construction of the double tubular concentrically oriented positive pressure breathing circuit of the present invention is illustrated. The circuit, which is generally referred to by the numeral 10 is shown to consist of an outer exhalation tube 12 and an inner inhalation tube 14. The outer tube 12 is shown to be of smooth walled construction, both along the exterior surface as well as the interior surface, and as illustrated in the preferred embodiment shown in FIG. 1 of the drawings, it is provided with an atomizing channel 16, formed by an outer peripheral wall 17, which together with a portion of the interior wall of the outer tube 12, forms the atomizing channel 16. The outer exhalation tube 12 terminates at a patient terminal end 18 which slip-fits over the exhalation housing member 20. The exhalation housing member 20 is shown to be formed by an outer tube member 21 and an inner tube member 22, the outer exhalation tube 12 slip-fitting over the terminal end of the outer tube member 21, as shown in FIG. 1 of the drawings. Where it is contemplated that the circuit of the present invention is to be formulated for disposable use, the fitting between the outer exhalation tube 12 and the outer tube member 21 of the housing member 20 may be bonded by any suitable means. Where the circuit is intended for reuseable use, the fitting between these two elements may be by way of a friction slip-fit or the like. The atomizing channel 16 extends the entire length of the outer exhalation tube 12 and interconnects with a source of pressurized fluid at the opposed end thereof, the source of pressurized fluid being either extraneous to the system, or forming a separate port in the ventilator.

The inner inhalation tube 14 is similarly shown to be of smooth walled construction and is also shown to have an inflation channel 24 formed by an outer peripheral wall 25, which together with a portion of the interior surface of the wall of the inner inhalation tube 14 forms the inflation channel 24. The inner inhalation tube 14 terminates at a patient terminal end 26 and seals with the inner tube member 22 of the housing member 20. Once again, the inflation channel 24 extends throughout the entire length of the inner inhalation tube 14, and connects at its opposed end with a separate port in the ventilator for providing a source of pressurized fluid for a purpose to be more fully defined hereinafter.

With respect to the exhalation housing member 20, as previously indicated, the member 20 is formed by the outer tube member 21 and the inner tube member 22. The outer tube member 21 also incorporates an housing atomizing channel 28 formed integrally therewith and constructed to matingly engage the atomizing channel 16 of the outer exhalation tube 12 again as depicted in FIG. 1 of the drawings. The housing atomizing channel 28 extends for a distance along the length of the housing member 20 and is turned 90° terminating in an outer peripheral neck 29 to accommodate a tube fitting thereabout. The housing member 20 is shown to be open at its inner end 30 and at the opposed end 31 it is closed by an end wall 32. Finally, the construction of the outer tube member 21 is completed by a circumferential groove 33 accommodating a circumferential shoulder 34 which forms a valve seat as will be more fully explained hereinafter.

The inner tube member 22 is shown to be provided with a housing inflation channel 36, which is constructed to mate with the inflation channel 24 of the inner inhalation tube 14. The housing inflation channel 36 is formed integrally with the inner tube member 22 and terminates in a port 37 which, in turn, establishes fluid communication with an inflation cuff 38, mounted circumferentially about the inner tube member 22. The outer peripheral ends of the cuff 38 are fixedly secured to the outer wall of the inner tube member 22, forming a fluid tight seal such that fluid cannot leak through the seal formed by the outer peripheral ends of the cuff 38. It is apparent that once the circuit is interconnected such that the housing inflation channel 36 is mated with the inflation channel 24 of the inner inhalation tube 14, a fluid flow path is established therethrough, through port 37, such that the inflatable cuff 38 may be inflated by the introduction therein of a fluid under pressure. The inner end 40 of the inner tube member 22 is shown to be open such that open fluid communication is established with the inner inhalation tube 14 when interconnected, and the outer opposed end 41 is shown to extend through an aperture provided in the end wall 32 of the housing 20 and provides a circumferential neck 42 for connection to a patient's face mask or mouthpiece M, as more clearly shown in FIG. 14 of the drawings.

It will also be observed that the inner tube member 22 is provided with a plurality of apertures 44 functioning for a purpose to be more fully described hereinafter. It will further be observed that the inner tube member 22 includes a downwardly depending neck 46 terminating in an atomizing port 47. The lower end of the neck 46 is fixedly secured to the inner surface of the outer tube member 21 in the same manner that the inner tube 22 is fixedly secured through the aperture provided in the end wall 32. Hence, it will be appreciated that the housing member 20 is formed as an integral unit, having the inner tube 22 fixedly secured within the outer tube member 21.

It will further be observed that a portion of the outer tube member 22 is provided with a U-shaped channel 48 (more precisely shown in FIGS. 5 and 6 of the drawings) which functions as the mounting means for mounting the nebulizer onto the outer tube member 21.

Insofar as the valving mechanisms are concerned it will be observed that the inner tube member 22 is provided with a flexible membrane 50 positioned thereabout, the membrane 50 being circumferentially positioned about the inner tube member 22. The membrane 50 forms a valve which seats against the circumferential shoulder 34 such that during the inhalation cycle by the patient negative pressure is created, forcing the membrane 50 against the shoulder 34 in fluid tight relationship. When positive pressure is exerted against the membrane 50, the membrane 50 will move away from the shoulder 34 and unseat, thereby permitting exhaled gases to flow therethrough.

Insofar as the inner tube member 22 is concerned, an inhalation valve 52 is provided formed by a circumferential ring 53 supporting a frusto-conical central rib member 54 centrally therein. The rib member 54 supports the flexible membrane 55, which is constructed to seat against the inner edges of the ring 53. Hence, when the flexible membrane 55 is seated against the inner edges of the ring 53, the valve member 52 is in the closed position. When gas is passed through the inner inhalation tube 14 and through the inner tube member 22 in the direction of the arrows 56, the flexible membrane 55 unseats from the peripheral edges of the ring 53, thereby permitting the gases to flow through the valve member 52, and on through the inner tube member 22, through the patient face mask M and hence to the patient.

It will be clear from the above description that the valve member 52 and the flexible membrane 50 function as an inhalation valve and an exhalation valve respectively. In other words, as gas is passed through the inner inhalation tube 14, in the direction of the arrows 56, the inhalation valve member 52 opens to permit the inhaled gases through to the patient. Simultaneously, negative pressure is created between the inner tube member 22 and the outer tube member 21, such that the flexible membrane 50 seats against the circumferential shoulder 34, in effect closing the exhalation valve while the inhalation valve member 52 is open. During the exhalation cycle, gases will pass initially into the inner tube member 22, but as the exhaled gases strike against the surface of the flexible membrane 55, the flexible membrane 55 will seat against the outer edges of the ring 53, closing the inhalation valve member 52. As the gases back up, they will flow through the apertures 44 and create positive pressure against the flexible membrane 50. This will then cause the flexible membrane 50 to open, thereby permitting gases to flow through the spacing between the inner tube member 22 n and the outer tube member 21. In this manner, unidirectional valve members are established for both the inhalation tube 14 and the exhalation tube 12.

Figure 2:
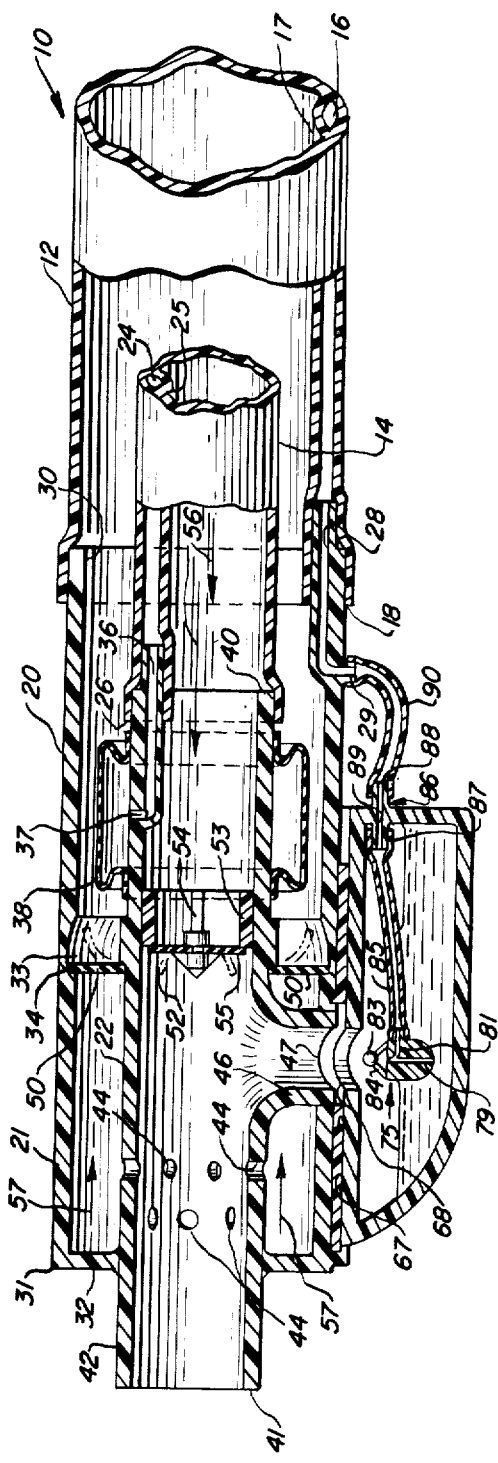
FIG. 2 is a side elevation view, partly in cross-section, showing the operation of the inflatable occlusion means incident to the present invention.

It should be noted that substantially the same effect produced by valve member 52 and membrane 50 may be achieved by location at any point along the exhaled gas path, such as port 107 in FIG. 10, and that the location of valve member 52 and membrane 50 as shown in FIG. 2 is only a preferred location for creating unidirectional flow in the exhalation tube portion of the circuit.

With regard to the inflatable cuff 38, as has been previously described, the inner tube member 22, is provided with the housing inflation channel 36 while the inner inhalation tube 14 is provided with the inflation channel 24. This channel 24 is in turn in fluid communication with a source of pressurized fluid, such as the ventilator provides and during the inhalation cycle when the ventilator cycles on, gases are introduced into the inhalation tube 14, and hence simultaneously down the inflation channel 24. The positive pressure created by the gas through the inflation channel 24 will inflate the cuff 38, thereby assuming the posture shown in FIG. 2 of the drawings. When fully inflated, the cuff will occlude the space between the inner tube 22 and the outer tube 21, and prevent the flow of gas in either direction. Hence, during the inhalation cycle, once the ventilator cycles on and the gas is simultaneously forced down the inhalation tube 14, gas also is forced down the inflation channel 24 to inflate the cuff 38. During this cycle, as previously described, the inflation valve member is open to permit incoming gas to flow to the patient, while the flexible membrane 50 is seated against the shoulder 34, closing the exhalation valve. It will be apparent that the purpose of the inflatable cuff 38 is to further ensure that there is no cross-contamination of the inhaled gases with exhaled gases, as well as to function as a positive resistance against any back pressure caused by the gases introduced into the system under pressure by the ventilator. It will further be clear that once the ventilator cycles off, such that gases are no longer being introduced under pressure through the inner inhalation tube 14, gas will also simultaneously cease to flow through the inflation channel 24, and hence, the inflatable cuff 38 will deflate and assume the posture as shown in FIG. 1 of the drawings. Therefore, during the exhalation cycle, when the ventilator is cycled off, it is clear that the flexible membrane 55 will be seated against the ring 53, thereby closing the inhalation tube 14 while simultaneously, the flexible membrane 50 will assume the open position as shown in the dotted lines in FIG. 1 while simultaneously, the inflatable cuff 38 deflates to assume the position as shown in FIG. 1, such that gases are permitted to flow down the exhalation tube 12.

Figure 4:
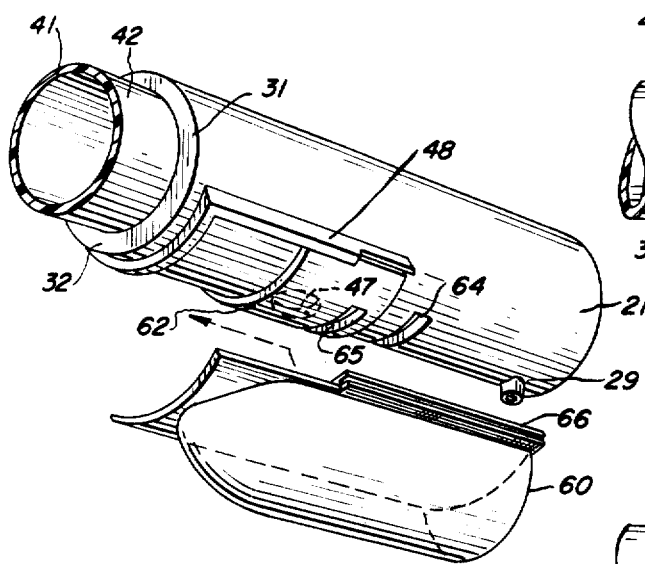
FIG. 4 is a perspective exploded view showing the patient receiving terminal end of the tubing circuit and the positioning of the nebulizer cartridge with respect to the exhalation tube thereof.
Figure 5:
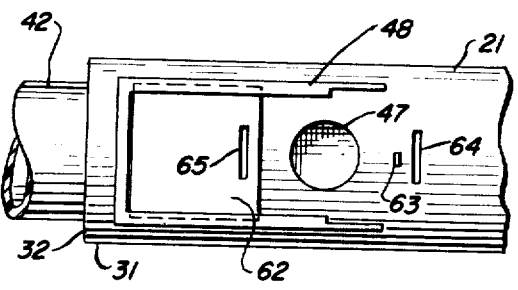
FIG. 5 is a bottom view showing the shuttering system formed as part of the outer wall of the exhalation tube and showing the shutter in the open position.
Figure 6:
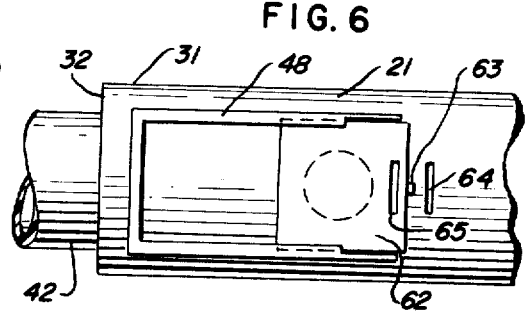
FIG. 6 is a bottom view of the tubing circuit, and specifically the outer wall of the exhalation tube, showing the slide mounting means for the nebulizer with the shutter in the closed position occluding the port in fluid communication with the inhalation tube.
Figure 9:
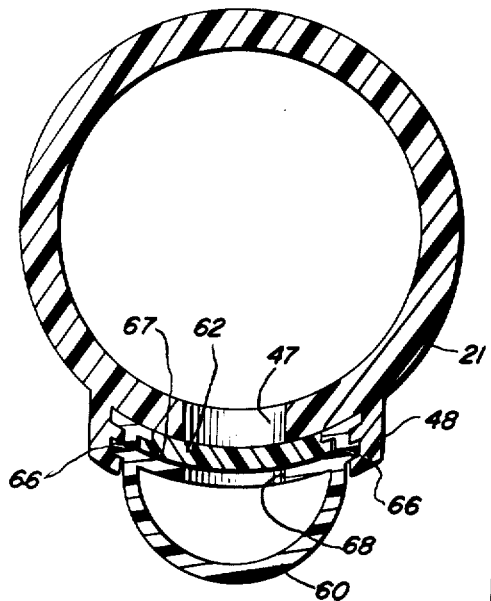
FIG. 9 is a side elevational cross-sectional view showing the exhalation tube with the nebulizer cartridge positioned therein in disengagably mounted relationship.

With reference to the details shown in FIGS. 1, 3, and 5 through 9 of the drawings, the construction of the outer tube member 21 and the relationship thereof, with the nebulizer is illustrated. As particularly shown in the exploded view in FIG. 4, the nebulizer 60 is formed as a separate cartridge and is constructed to be easily insertable and mountable on the outer tube member 21. As previously indicated the outer tube member 21 is provided with a U-shaped channel 48 which surrounds the atomizing port 47. Positioned within the channel 48 is a slidable shutter 62, which slides along the outer surface of the outer tube member 21 such that the shutter 62 may alternately open and close the atomizing port 47. The shutter is permitted to slide laterally until it meets the stop boss 63 as depicted in FIG. 6 of the drawings. Further, the outer tube member 21 is shown to be provided with a longitudinal slot 64, while the slidable shutter 62 is provided with a similar door slot 65.

Figure 7:
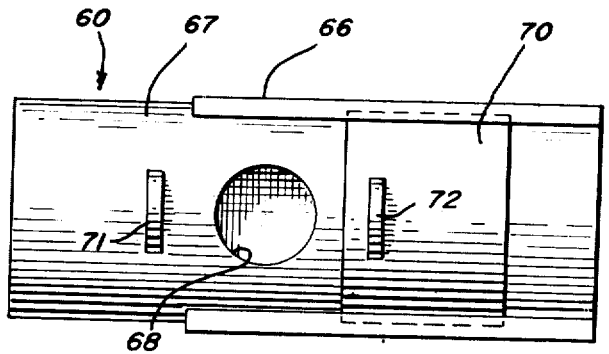
FIG. 7 is a top view of the nebulizer cartridge showing the shutter in the open position.
Figure 8:
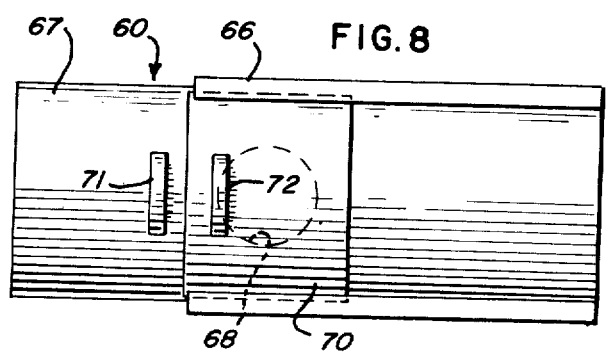
FIG. 8 is a top view of the nebulizer cartridge showing the shutter in the closed position.

The nebulizer cartridge 60 is shown to be semi-elliptical in configuration and includes a pair of end rails 66 which are designed to slidably engage within the U-shaped channel 48 in order to mount the cartridge onto the outer tube member 21. As shown in FIG. 7 and 8 of the drawings, the top portion of the cartridge 60 is closed by a top wall 67, having an outlet port 68 positioned therein. The positioning of the outlet port 68 with respect to the top wall 66 is constructed such that when mounted on the outer tube member 21, the outlet port 68 is in registry with the atomizing port 47 of the housing member 20. It will further be observed that the outlet port 68 may be alternately opened and closed by means of a sliding door 70 mounted on the top wall 67 of the cartridge 60. The top wall 67 also includes a cartridge flange 71, while the sliding door 70 includes a door flange 72, the cartridge flange 71 and door flange 72, being in upstanding relationship with respect to the top wall 67 thereof. It now becomes apparent by viewing FIGS. 5 through 8 of the drawings, that in order to slidably mount the nebulizer cartridge 60 onto the outer tube member 21, the operator positions the cartridge 60 such that the cartridge flange 71 is inserted within the door slot 65 while the door flange 72 is positioned within the longitudinal slot 64. In addition, the catridge 60 is positioned such that the end rails 66 mate with the U-shaped channel of 48. Hence, as the operator then pushes the cartridge 60 forward, the cartridge flange 71 will cause the slidable shutter 62 to move from the closed position as shown in FIG. 6 of the drawings, to the open position as shown in FIG. 5 of the drawings, while simultaneously, the longitudinal slot 64 will retain the door flange 72, thereby slidably moving the sliding door 70 opening the outlet port 68 as the atomizing port 47 is being similarly opened. Once the cartridge 60 has been fully inserted within the U-shaped channel 48, the atomizing port 47 will be in vertical registry with the outlet port 68 such that fluid communication is established between the nebulizer cartridge 60 and the inner tube member 22. The relationship described is clearly illustrated in FIG. 9 of the drawings.

Figure 3:
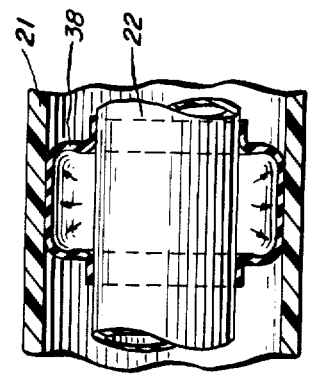
FIG. 3 is a side elevational view, partly in cross-section, showing the capillary tube system of the nebulizer incident to the present invention.

It will be apparent in view of the above description that the provision of a cartridge style nebulizer in conjunction with an outer tube member, both of which are provided withh slidable doors, or shutters, permits an operator to handle a prefilled sterile nebulizer without violating the sterile conditions established therein while at the same time permitting ease of handling and quick installation and mounting of the nebulizer onto the respiratory circuit. Insofar as the interior portion of the nebulizer is concerned, the detailed features of the atomizing head are shown in FIGS. 1 and 3 of the drawings. It will be observed that the present invention provides an improved atomizing system according to the following description.

As shown in the details of FIG. 3 of the drawings, the atomizer 75 is illustrated. It will be noted that the atomizer 75 is formed by a flotation head 77, provided with a fluid channel 79, extending through the center portion thereof. The floatation head 77 is further provided with a gas pressure channel 81, which meets with and is in fluid communication with the fluid channel 79 at its inner end and extends outwardly from the floatation head 77 to form a connecting neck 82, externally of the floatation head 77. The atomizer 75 is completed by an atomizing head 83, carried on the top portion of the floatation head 77, by means of support struts 84. The atomizing head 83 is positioned to be immediately above the fluid channel 79 and functions to fracture the fluid as the same is aspirated up the fluid channel 79 into striking engagement with the atomizing head 83.

The flotation head 77 functions to float on the surface of the fluid contained within the nebulizer 60 and interconnects with the outer portion of the nebulizer 60 by means of a pressure transmission tube 85. It will be observed that the nebulizer cartridge 60 is provided with a longitudinal connector 86, having an inner connecting port 87 and an outer connecting port 88, with a gas channel 89 traversing therethrough. Fluid communication is completed by a second gas transmission tube 90, which interconnects between the outer connecting port 88 and the peripheral neck 29, all as illustrated in FIG. 1 of the drawings. It will therefore be appreciated that fluid communication is established through the atomizing channel 16, the housing atomizing channel 28, through the peripheral neck 29, second gas transmission tube 90, and hence through the longitudinal connector 86 and via the gas transmission tube 85, whereby gas is caused to enter through the flotation head 77 via the gas pressure channel 81. In operation as the gas source is cycled on and gas enters through the atomizing channel 16, the gas will enter into the floatation head 77, via the gas pressure channel 81 and cause negative pressure in the fluid channel 79, causing fluid to rise up through the fluid channel 79, under pressure, and fracture when striking the atomizing head 83. In this manner a fine mist of the fluid contained within the nebulizer cartridge 60 is obtained which is then permitted to enter through the outlet port 68 of the cartridge 60, and thence through the atomizing port 47 and into the inner tube member 22 for inhalation by the patient. Obviously, atomizing of fluids within the nebulizer cartridge 60 will only occur during the inhalation cycle such that when the ventilator is cycled on and positive gas pressure is established through the inner inhalation tube 14, the source of the gas pressure for the atomizing channel 16 also cycles on, such that the nebulizer cartridge 60 will function to produce an atomized spray of medicinal fluids into the inner tube member 22, for inhalation by the patient.

It now becomes apparent from the above description relative to the atomizing head that a novel and simplified atomizing system has been provided which ensures complete atomization of the medicinal fluids contained within the nebulizer cartridge 60. By providing a floatation type atomizer, the device will function properly regardless of the liquid level within the nebulizer cartridge. Furthermore, even should the circuit, as a whole, become cocked for whatever reason the floatation head 77 of the atomizer 75 will continue to ride on the surface of the fluid and will continue to supply atomized medicinal fluids into the inhalation tube for inhalation by the patient.

Insofar as the nebulizer cartridge 60 itself is concerned, it is also apparent that the number of components have been reduced and simplified, while at the same time permitting refilling of the nebulizer under sterile conditions which will be maintained intact during shipment, installation, and removal.

With regard to FIGS. 10 and 14 of the drawings, the opposed end of the respiratory breathing circuit of the present invention is illustrated. With specific reference to FIG. 10 of the drawings, it will be observed that the opposed end of the circuit 10 is provided with a tailpiece 100 formed by an outer sleeve 101, and an inner sleeve 102. It will be appreciated that the outer sleeve 101 is open at its inner end and is closed at its outer end by an end wall 103, having the inner sleeve 102 extending outwardly through an aperture provided in the end wall 103. Furthermore, the lower portion of the outer sleeve 101 is shown to have a T-shaped arm 104 extending downwardly therefrom, but formed integrally therewith, the lower portion of the arm 104 having a collection port 105 formed therein which may be conveniently occluded by stopper member 106. The inner portion of the outer sleeve 101 is further shown to be provided with a gas atomizing channel 108, terminating in a port 109 which serves as the connection point to the atomizer gas source at the ventilator. As is shown in FIG. 10 of the drawings, the outer exhalation tube 12 is fitted over the inner end of the outer sleeve 101 such that the atomizing channel 16 of the tube 12 fits over the gas atomizing channel 108 thereby establishing fluid communication between the gas atomizing channel 108 and the atomizing channel 16.

The inner sleeve 102 is fixedly held in concentric orientation with respect to the outer sleeve 101 since the inner sleeve 102 is fixedly secured through the aperture provided in the end wall 103 of the outer sleeve 101. Again, the inner sleeve 102 is designed to fit within the inner inhalation tube 14 at its inner end and having the opposed end extending outwardly from the end wall 103 for a short distance. With respect to the inner end of the inner sleeve 102, it will be observed that the inner sleeve 102 is provided with a gas inflation channel 110 formed integrally therewith and terminates in an outer port 112 adapted for interconnection with a source of fluid under pressure at the ventilator. As shown in FIG. 10, once the inner inhalation tube 14 is mounted on the inner end of the inner sleeve 102, the inflation channel 24 of the inner inhalation tube 14 is in fluid communication with the gas inflation channel 110 of the inner sleeve 102. Hence, once the outer port 112 is connected to a source of pressurized fluid, such as a separate port of the ventilator (not shown) pressurized fluid travelling through the gas inflation channel 110 ultimately is introduced into the inflatable cuff 38, thereby to inflate the same and occlude the space between the inner inhalation tube 14 and the outer exhalation tube 12, as more clearly shown in FIGS. 1 and 2 of the drawings. The outer end of the inner sleeve 102, extends outwardly from the end wall 103, for a short distance and it is designed as a connection point for tubing 113, which interconnects the inhalation tube 14 with the humidifier 115. The details of the improved novel form of the humidifier 115 provided by this invention will be discussed hereinafter.

Insofar as the interconnections between the outer exhalation tube 12 and the outer sleeve 101 are concerned, as well as the interconnection between the inner inhalation tube 14, and the inner sleeve 102, these fittings may be of the friction-fit slip-type fittings or may be fixedly secured by any suitable adhesive or bonding means. The use of the respectively different fittings is dependent primarily upon whether the circuit as a whole is designed as a disposable circuit, or as a reusable circuit.

FIG. 10 of the drawings also illustrates an improved form of a humidifier 115, provided by this invention. It will be observed that this humidifier 113 is provded with an outer wall 117 which accommodates an outlet port 118 as positioned in the top wall thereof. A water chamber 120 is provided in the interior portion of the humidifier 115 and separated from the outer wall 15 by an inner wall 121, which is spaced from the outer wall 117 along the sides and bottom of the humidifier 115. It will further be observed that adjacent the bottom portion of the humidifier 115 the outer wall 117 is provided with an inlet port 123 which is in fluid communication with the heating chamber 119 formed by the space between the inner wall 121 and the outer wall 117 of the humidifier 115. Opposite to the inlet port 123, and located adjacent the top portion of the humidifier 115, is an exhaust port 125. The humidifier 115 is completed by a gas tube 127, which extends downwardly through the top wall of the humidifier 115 to a point adjacent the lower portion of the water chamber 120. The outer end of the gas tube 127 functions as a connector neck 128, and accommodates a slip-fit friction fitted tube thereabout.

It will now be appreciated that as an additional feature of the present invention, the novel humidifier provided in this invention permits a more complete utilization of the heat present in the exhaled gases to render the system energy conservative. It will be observed that an exhalation gas tube 130 interconnects the exhaled gas port 107 of the T-shaped arm 104 with the inlet port 123, such that exhaled gases flowing down the outer exhalation tube 12 and through the outer sleeve 101 of the tailpiece 100, will be exhausted through the T-shaped arm 104 and enter into the heating chamber 119 of the humidifier 115, via the inlet port 123. Since the exhaled gases are generally of a temperature slightly less than body temperature at the time the gases enter the heating chamber 119 of the humidifier 115, the heat incident to such exhaled gases may then be utilized to heat the water contained in the water chamber 120 of the humidifier 115. Additionally, it should be noted that additional devices to remove heat from the exhaled gas, such as fins or heat conductive materials such as metallic wools, may be located in the chamber 119, and the inclusion of such should be considered as within the scope of this novel system. A constant flow of exhaled gases is permitted by entering into the heating chamber 119 through the inlet port 123 and exhausting through the exhaust port 125. The gas for inhalation is routed from the ventilator through the gas tube 127 and bubbled through the water in the humidifier 115. The gases will rise through the water and exit from the humidifier through the outlet port 118 and hence into the inner sleeve 102 of the tailpiece 100, through the tubing 113. As has been previously indicated, the system contemplated by this invention is a positive pressure breathing circuit and since the gas from the ventilator is under positive pressure, the gas will be forced through the system in the manner indicated. Once gas is introduced into the inner sleeve 102, of the tailpiece 100, the gas will flow on through the inner inhalation tube 14 and ultimately to the patient. The overall system is clearly shown in FIG. 14 of the drawings, which shows the forward end of the system accommodated with a face mask M which is positioned over the patient's mouth and nose.

Figure 14:
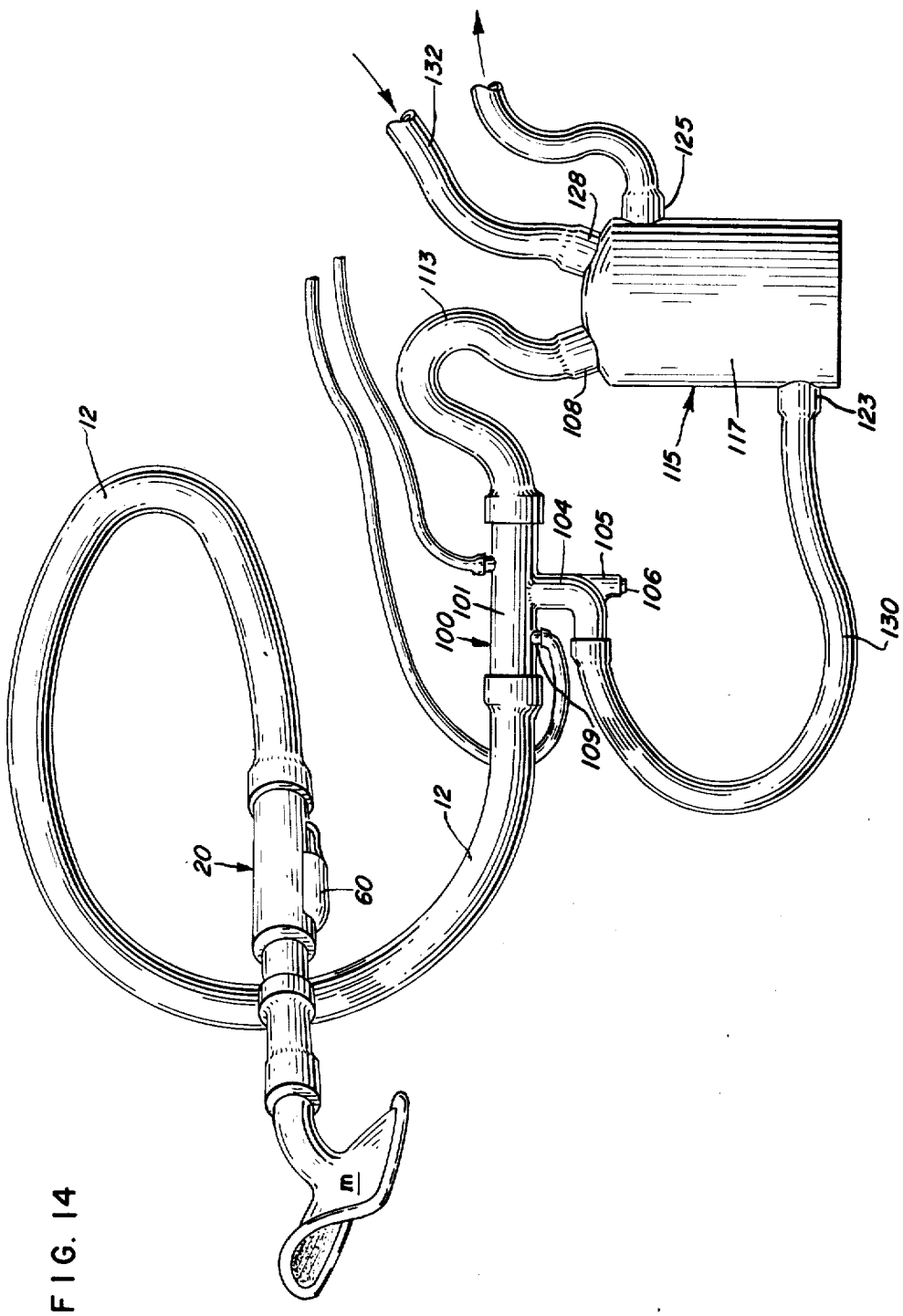
FIG. 14 is a perspective view of the system employing the circuit of the present invention and the interconnection thereof with a patient face mask at the patient receiving terminal end and connected to the humidifier at the opposing end of the circuit.

With reference to FIG. 14 of the drawings, wherein the overall system is illustrated, with the exception that the ventilator is not shown. It is now apparent the manner in which the circuit 10 of the present invention operates. As previously indicated, the humidifier is in fluid communication with the ventilator through the ventilator tubing 132, wherein gases from the ventilator under positive pressure enter into the humidifier through the gas tube 127, thereby to be bubbled through the water in the humidifier 115. Once the gases are bubbled through the water, the gases will enter into the circuit 10 through the tubing 113 and hence, be forced through the inner sleeve 102 of the tailpiece 100 and on into the inner inhalation tube 14 of the circuit 10. The gases will then be forced through the face mask M and permit respiration by the patient. With reference to FIG. 1 of the drawings, unidirectional gas flow in the direction of the arrows 56 is established by means of the unidirectional inhalation valve 52 during the inhalation cycle. Simultaneously, the gas inflation channel 110 as well as the inflation channel 24 of the inner inhalation tube 14 is in fluid communication with a separate port on the ventilator through the outer port 112. The gas source is synchronized with the ventilator such that when the ventilator cycles on, not only will gas be forced through the humidifier 115 and into the inner inhalation tube 14, but gas under pressure will also be forced through the port 112 into the gas inflation channel 110 and on into the inflation channel 24, which is in turn, in fluid communication with the inflatable cuff 38. Hence, during the inhalation cycle, the inflatable cuff 38 will be caused to inflate, thereby occluding the space between the inner inhalation tube 14 and the other exhalation tube 12. The cuff then functions as a resistance to any back pressure incident to the circuit 10 during the inhalation cycle and prevents any cross-contamination of inhaled gases with exhaled gases, as well as to ensure the operation of the circuit 10 as a positive pressure breathing device.

Also on a simultaneous basis, gas under pressure is fed into the atomizing gas channel 108, through the port 109, which as shown in FIG. 14 of the drawings, is in fluid communication again, with the gas under pressure. This gas is then directed to the nebulizer cartridge 60, via the atomizing channel 16 and through the appropriate channels provided in the housing member 20, and through the first and second gas transmission tubes 85 and 90 respectively. This gas will then enter into the floatation head 77 through the gas pressure channel 81 and create negative pressure in the fluid channel 79. This negative pressure will then draw the fluid in the nebulizer cartridge 60 up through the fluid channel 79 and will be fractured when striking against the atomizing head 83. In this manner, a fine mist of medicinal fluids is created and will be forced up into the inhalation tube 14, through the atomizing port 47, provided therein. Hence, it will be appreciated that once positive pressure is established for the circuit 10, positive gas pressure is established for the inner inhalation tube 14, as well as into the inflation channel 24, and the atomizing channel 16.

During the exhalation cycle, the ventilator cycles off, such that gases will cease flowing through the inhalation tube 14, and will further cease flowing through the atomizing channel 16, and further, will cease flowing through the inflation channel 24. Hence, during the exhalation cycle, the atomizing of the medicinal fluids ceases and the inflatable cuff 38 deflates and as the patient exhales, the unidirectional inflation valve 52, will close while the flexible membrane 50 will be forced to the open position, and as the exhaled gases then enter into the inner tube member 22, the gas will be forced through the apertures 44 and enter into the outer exhalation tube 12. The pressure of the exhaled gases, of course forces the flexible membrane 50 into the open position and since the inflatable cuff 38 has now deflated, the exhaled gases are permitted to pass down the outer exhalation tube 12, and ultimately through the outer sleeve 101 of the tailpiece 100.

From a view of FIG. 10 of the drawings, it will be appreciated that the exhaled gases may be directed to the heating chamber 119 of the humidifier 115 through the exhalation gas tube 130 and will enter into the chamber 119, through the inlet port 123. Again, as indicated previously, the exhaled gases are in a heated condition and this heat may then be utilized to heat the water contained in the water chamber 120, of the humidifier 115. The exhaled gases will travel through the heating chamber 119 and exhaust through the exhaust port 125, usually to atmosphere, or to a device to measure the volume of gas exhaled by the patient.

As has been indicated previously, one of the difficulties which has been encountered is the condensation of moisture in the circuit from the gases which has been heated and humidified. As has been indicated, the gases tend to cool during the travel from the humidifier to the patient, and as the gases cool, a rain-out of moisture does occur. It is apparent from the present invention that by providing a double tubular concentrically oriented configuration for the inhalation tube 14 and the exhalation tube 12, a heat exchanger effect has been created and the exhaled gases passing through the exhalation tube 12 maintain the elevated temperature of the gases passing from the inhalation tube 14, without any extraneous source of heat. In this manner, the amount of rain-out of moisture of the heated gases passing to the patient is not completely eliminated but at least minimized such that the gases will remain at an elevated temperature and completely humidify on entering the patient. To the extent that any rain-out does occur, the inhalation tubing may be drained as is the present practice. Should any condensation occur in the exhalation tube it may be removed through the collection port 105 which is shown occluded by stopper member 106 in FIG. 10. It has been found, however, that the amount of rain-out of moisture from the inhaled and exhaled gases is very minimal with this novel system, however, it is recognized that over a long period of continued use of this system, in respiratory therapy, some rain-out may occur and drainage of this moisture is accommodated by incorporating the collection port 105 as indicated in FIG. 10 of the drawings.

With reference to FIGS. 11 through 13 of the drawings, various embodiments of tubing are contemplated within the scope of the present invention. IN both respiratory as well as anesthesia circuits of the type presently available, corrugated tubing of the type illustrated in FIG. 11 of the drawings, has been utilized. The drawback incident to corrugated tubing is that the corrugated interior surfaces present an interior surface to the gases which creates turbulence since the gases have a tendency to strike against all the various corrugated surfaces and hence, cause turbulence therein. The result of turbulence is the fact that the gases are more likely to cool and a significant amount of moisture rain-out then occurs. In addition, the spaces incident to the corrugated tubing provide breeding places for bacteria and hence, due to the inherent difficulty of cleaning and sterilizing corrugated tubing, the possibility of bacterial infection is prevalent. However, with reference to FIG. 11 of the drawings, it is contemplated that corrugated tubing can be utilized in connection with the present invention. It will be observed that there is provided an inner corrugated tube 140 which is concentrically disposed with respect to an outer corrugated tube 142. The concentric orientation may be maintained by providing the circuit with suitable spacer members (not shown) to hold the inner and outer tubes in spaced and concentrically oriented position. This type of structure is disclosed in my co-pending application Ser. No. 437,033 entitled ANESTHESIA CIRCUIT and filed in the name of Bernard Paluch on Jan. 28, 1974. The significance of FIG. 11 of the drawings is the fact that corrugated tubing of the type presently available may be utilized within the scope and purview of the present invention.

Similarly, FIG. 12 shows another more preferred embodiment wherein an inner tube 145 is provided functioning as the inner inhalation tube and an outer tube 147 is provided functioning as the exhalation tube. Both the inner tube 145 and the outer tube 147 are of smooth walled construction, thereby minimizing the surfaces against which the gases strike as they flow through the tubing and minimizing, thereby, gas turbulence. In this embodiment, it will be noted that a helically wound wire 148 is provided about the inner inhalation tube 145 in order to provide rigidity and stability. Spacer members (not shown) may similarly be used in order to maintain the spaced and concentric orientation of the tubes 145 and 147 respectively.

Again, with reference to FIG. 11 of the drawings, and in this embodiment of the invention, the outer corrugated tube is shown to be provided with a loose and separate atomizing tube 143, while the inner corrugated tube 140 is similarly provided with a loose and separate inflation tube 144. The tubes 143 and 144 respectively, function in the manner described with respect to the gas atomizing channels 16 and inflation channel 24 with reference to FIG. 1 of the drawings. The embodiment in FIG. 12 of the drawings similarly contains an atomizing tube 149 which is loosely positioned within the outer exhalation tube 147, and inflation tube 150 which is provided as a separate and loose fitting tube within the inner inhalation tube 145.

FIGS. 13 represent the preferred embodiment of the invention wherein the tubing is illustrated as being extruded as smooth walled tubing having an outer exhalation tube 155 of smooth walled construction and an inner inhalation tube 157, of similarly smooth walled construction. It is further contemplated that the atomizing channel 158 may be formed integrally with the outer exhalation tube 155 when extruding the same, and similarly, the inflation channel 159 may be formed integrally with the inner inhalation tube 157, when extruding the same. Hence, in this embodiment of the invention there is no requirement or necessity to have separate tubes positioned within either the outer exhalation tube or the inner inhalation tube in order to accommodate the atomizing channel and inflation channel as previously described. In addition, the problems incident to corrugated tubing have been eliminated, and further, the problems incident to gas turbulence which would be encountered by the embodiment illustrated in FIG. 12 of the drawings is similarly avoided.

Figure 15:
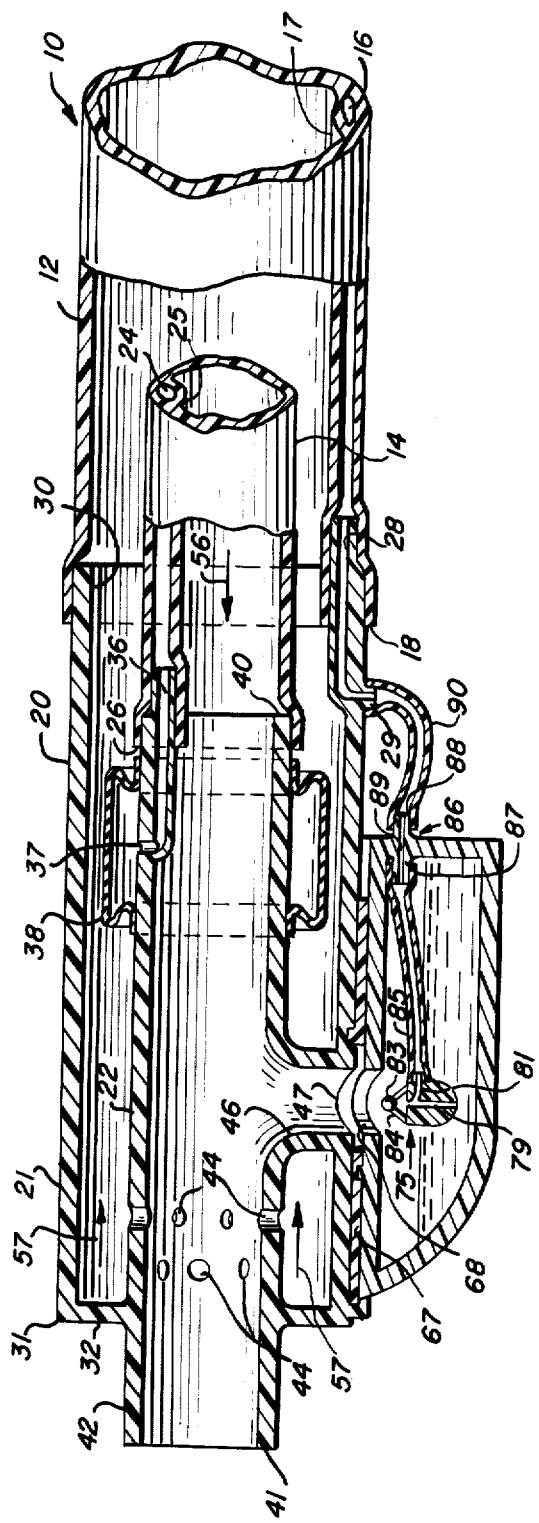
FIG. 15 is a side elevational cross-sectional view of an alternative embodiment of the Positive Pressure Breathing System of the present invention, wherein the unit directional valves positioned in the inhalation and exhalation lines respectively are eliminated, and the inflatable cuff member acts as a valving means for the system.

With reference to FIG. 15 of the drawings, it will be observed that an alternative embodiment of the subject Positive Pressure Breathing System contemplates that the inhalation and exhalation valves may be eliminated from the system entirely. As will be observed in the embodiment shown in FIG. 15, the inhalation valve (52 in FIG. 1) has been eliminated with respect to the inner tube member 22, and the flexible membrane (50 in FIG. 1) has been eliminated from the outer tube member 21. In this embodiment, therefore, the inflatable cuff 38 operates as the sole valving means for the system. Hence, once the ventilator cycles on and gas is introduced down the inhalation tube 14, and also down the inflation channel 24, the cuff 38 is inflated and functions to prevent cross contamination of inhaled gases with exhaled gases. It will, therefore, be appreciated that during the inhalation cycle, gas will flow down the inhalation tube 14, while simultaneously the cuff 38 is in the inflated position to occlude the space between the outer tube member 21 and the inner tube member 22 such that the inhalation gas necessarily passes down the inner tube to the patient supported apparatus such as the face mask. Once again, since the inflatable cuff 38 is positioned adjacent the patient terminal end of the system, there is only a minimal amount of exhaled gas present in the system to add mix with any inhaled gases such that any danger of the patient breathing exhaled gases is minimized.

It will also be obseved that once the ventilator cycles off such that gases are no longer forced down the inhalation tube 14, similarly, gas is no longer forced down the inflation channel 24 such that the cuff 38 is permitted to deflate. It will be appreciated that the subject Positive Pressure Breathing System of the present invention is employed in connection with apparatus such as a ventilator or the like, which has in addition thereto, in most circumstances, a humidifying device for humidifying the inhaled gases. It is further to be appreciated that when a ventilator cycles to the off position, a column of gas remains in the inhalation tube, and furthermore, the ventilator does not permit the backflow of gas through the same. Hence, during the exhalation cycle, as exhaled gas is passed into the inner tube 14 from the patient supported face mask, the pressure exerted by the patient during exhalation will cause a compression of the gases existing within the inhalation tube thereby causing a back pressure to exist with regard to the gases exhaled by the patient. This back pressure will force the exhaled gases through the apertures 44 in the inner tube 14 and into the outer tube member 21 for exiting down the outer exhalation tube 12. As indicated previously, the exhaled gases are permitted to pass the cuff 38 since the cuff 38 is now in a deflated condition during the exhalation cycle. Once again, when the ventilator cycles to the on position during the inhalation cycle, the cuff 38 immediately inflates thereby occluding the outer exhalation tube 12 such that gases are now once again forced down the inhalation tube 14 for inhalation by the patient.

The alternative embodiment as described in FIG. 15 of the drawing will therefore obviously operate in the manner intended by the present invention in spite of the elimination of the inhalation and exhalation valves (52 and 50 respectively), for the reason that the ventilator machine itself will operate as the valve due to the column of gas remaining in the system and being compressed by the exhaled gases exhaled by the patient. It will be appreciated that the preferred embodiments of the invention are shown in FIGS. 1 through 14 of the drawings, but nevertheless, the invention will operate adequately in the manner described above with reference to FIG. 15 of the drawings.

In summarizing the inventive aspects of the invention described herein, it is apparent that there has been provided a positive pressure respiratory circuit, which is formed from a double tubular concentricaly oriented inhalation tube and exhalation tube. This construction provides a heat exchanger effect, thereby to permit the maintenance of the heat and humidity level of the gas as the same travels down the inhalation line prior to inhalation by the patient. In addition, the means for providing the resistance to back pressure has been incorporated into the circuit by way of an inflatable cuff which inflates during the inhalation cycle once the ventilator is cycled on. Furthermore, the nebulizer has been incorporated into the system as a prefilled sterile and disposable cartridge which may be easily inserted and mounted onto the circuit, by providing an outer exhalation tube having a shutter occluding a port, and similarly providing the nebulizer cartridge with a port occluded by a doorway or shutter, the operator may easily slidably mounted the nebulizer cartridge onto the outer exhalation tube, causing the respective shutters to open and establish fluid communication between the nebulizer and the inhalation channel.

With regard to the nebulizer it is further apparent that this invention provides a simplified and improved atomizing system for the nebulizer to ensure that regardless of the positioning of the nebulizer, or the circuit as a whole, the medicinal fluids contained within the nebulizer will become atomized during the inhalation cycle. Once again, the atomizing channel in fluid communication with the atomizing head of the nebulizer is constructed to be incorporated within the system and in fluid communication with a source of gas under pressure. This source of gas is similarly cycled with the ventilator such that when the ventilator does cycle on, gas will be provided for the inhalation channel, as well as gas being provided to atomize the medicinal fluids in the nebulizer and the inflatable cuff will inflate, all simultaneously. On the other hand, during the exhalation cycle, the reverse occurs, since the inflatable cuff will be caused to deflate as the gas flow in the inflation channel is interrupted and similarly, the nebulizer will cease atomizing when the gas flow in the atomizing channel is similarly interrupted. Additionally, by providing unidirectional or valving means for both the inhalation tube and exhalation tube, exhaled gases cannot enter the inhalation tube and therefore are directed and guided into the exhalation tube which will only permit one-way gas flow in countercurrent direction with respect to the flow of gas down the inhalation tube. It is this feature which provides the heat exchanger effect, since the exhaled gases are generally at body temperature and will therefore heat down the entire length of the tubing circuit.

In addition to the above, the system contemplates the further use of the exhaled gases to heat the water in the humidifier. This is accomplished by interconnecting the exhalation tube with the heat chamber of a humidifier such that the heat of the exhaled gases may be further utilized to the fullest extent possible in order to heat the water in the humidifier.

While moisture rain-out is minimized due to the novel construction of the present circuit, nevertheless the system also permits drainage of any moisture should rainout occur by providing a collection port in an appropriate location such that drainage of moisture is permitted under those conditions where the circuit is used for a long period of time as some moisture condenses within the tubing circuit.

The provision of smooth walled tubing having both the inflation channels and atomizing channels integrally formed therewith further resulting in improved features since gas turbulence is minimized and breeding places for bacteria and viruses is minimized or completely eliminated. It is relevant to appreciate the fact that the present circuit may be utilized in connection with existing corrugated tubing as well as with smooth walled tubing and hence, the system may be employed in connection with existing equipment and with existing materials.

While there has been described what is considered to be the preferred embodiment of the invention, various modifications may be made therein without departing from the true spirit and scope of the invention. All such obvious modifications and variations are intended to be covered, by the appended claims herein.

I claim:

1. An a positive pressure breathing circuit for operation in conjunction with a positive pressure ventilator and interposed btween the ventilator and a patient-supported device such as a patient connection means, useful in conjunction with respiratory therapy, the improvement comprising in combination, a concentrically oriented inhalation/exhalation circuit having an inner inhalation tube and an outer exhalation tube, said outer exhalation tube being spaced from and concentrically oriented with respect to said inner inhalation tube positioned therein, said inner inhalation tube having a patient receiving terminal at one end thereof and a gas source terminal at the opposed end thereof in fluid communication with the positive pressurized source of said ventilator, said outer exhalation tube having a patient receiving terminal at one end thereof and an exhaust end at the opposed end thereof, said inner inhalation tube and said outer exhalation tube being in fluid communication with the ventilator during the inhalation and exhalation breathing cycles respectively, inflatable occlusion means interposed between said inner inhalation tube and said outer exhalation tube and in fluid communication with said positive pressurized source of said ventilator such that said inflatable during the inhalation phase occlusion means is alternatively inflatable and deflatable during the exhalation phase in response to fluid pressure from the source thereof, the gas flow in said inhalation tube being countercurrent with respect to the gas flow in said exhalation tube thereby to stabilize and maintain the temperature of the gas within said inner inhalation tube without any extraneous source of heat, while at the same time permitting inflation of said inflatable occlusion means during the inhalation cycle thereby to prevent the admixture of inhaled gases and exhaled gases during the inhalation cycle while concomitantly permitting the exhausting of exhaled gases through the system, said ventilator functioning to create a gas back pressure in the inhalation tube during the exhalation cycle thereby to force exhaled gases to exhaust from the system through the exhalation tube due to the fluid gas pressure created therein, whereby gas suitable for patient inhalation enters said circuit through said inner inhalation tube under positive pressure to be received by the patient during which time said inflatable occlusion means is fully inflated and interposed between said inner inhalation tube and said outer exhalation tube to prevent the admixture of inhaled gases with exhaled gases, while resisting any back pressure existing in said circuit, while exhaled gases exhaled by the patient are forced initially into said inhalation tube and are caused by the back pressure existing in said inhalation tube to exit through said exhalation tube, said occlusion means being deflated during the exhalation cycle to permit the exhausting of exhaled gases therethrough.

2. The positive pressure breathing circuit as set forth in claim 1 above, wherein said inner inhalation tube is provided with a plurality of apertures between said patient receiving terminal end and said inflatable occlusion means to permit fluid communication between said inner inhalation tube and said exhalation tube, whereby upon exhalation, exhaled gases are forced by the gas back pressure existing in said inhalation tube to exit through said plurality of apertures and exhaust from said circuit through said exhalation tube.

3. The positive pressure breathing circuit as set forth in claim 1 above, wherein said inflatable occlusion means comprises an inflatable cuff fixedly secured to the outer surface of said inner inhalation tube, means for providing fluid communication between said inflatable cuff and said source of fluid under pressure, such that when pressurized, said inflatable cuff will inflate and bear against the interior surfaces of said outer exhalation tube and occlude the space between said inner inhalation tube and said outer exhalation tube, thereby to prevent cross contamination and admixture of gases as between the inner inhalation tube and the outer exhalation tube as well as to provide a resistance against any back pressure caused during said inhalation cycle.

4. The positive pressure breathing circuit as set forth in claim 3 above, wherein said inner inhalation tube is provided with a separate inflation channel positioned interiorly thereof and in fluid communication with said inflatable cuff at the inner terminal end of said channel and in fluid communication positive pressurized source of said with the ventilator at the opposed end of said channel whereby the introduction of fluidized pressure into said channel will result in the inflation of said inflatable cuff at the opposed end of said channel thereby to occlude the space between said inner inhalation tube and said outer exhalation tube.

5. The positive pressure breathing circuit as set forth in claim 4 above, wherein said inflation channel is formed integrally with said inner inhalation tube and formed as a separate channel therein.

6. The positive pressure breathing circuit as set forth in claim 1 above, wherein said circuit further includes nebulizer means disengageably mountable upon said outer exhalation tube and in fluid communication with said inner inhalation tube such that atomized medication may be introduced into said inner inhalation tube during the inhalation cycle and gas under positive pressure is introduced therein for inhalation by the patient.

7. The positive pressure breathing circuit as set forth in claim 1 above, wherein said circuit further includes gas humidification means in fluid communication with and interposed between said inner inhalation tube and said gas source for said inner inhalation tube, said gas humidification means including a water chamber therein for providing a source of humidity for gases which pass therethrough, said water chamber being surrounded by a heating chamber, said heating chamber being in fluid communication with said outer exhalation tube, whereby gas suitable for patient inhalation is first passed through said gas humidification means thereby to humidify the gas prior to entry into said inner inhalation tube, and exhaled gases are passed into said heating chamber surrounding said water chamber, thereby to utilize the heat contained in the exhaled gases to heat the water contained in said water chamber.

8. The positive pressure breathing circuit as set forth in claim 1 above, wherein said circuit further includes a drainage collection port in fluid communication with said outer exhalation tube, said drainage collection port including moveably engageable stopper means whereby removable of said stopper means permits manual removal of any fluids collected within the circuit.

9. The positive pressure breathing circuit as set forth in claim 1 above, which further includes an inflation channel positioned within said inner inhalation tube and having one end in fluid communication with said inflatable occlusion means on the opposed end thereof in fluid communication with said source of gas under pressure, whereby during the inhalation cycle as gas under pressure is forced through said inhalation tube, gas is similarly forced through said inflation channel thereby to inflate said inflatable occlusion means.

* * * * *

UNITED STATES PATENT OFFICE
CERTIFICATE OF CORRECTION

Patent No. 3,945,378          Dated March 23, 1976

Inventor(s) Bernard R. Paluch

It is certified that error appears in the above-identified patent and that said Letters Patent are hereby corrected as shown below:

In Column 2, line 27, delete " ' " and insert -- ° --

In Column 15, the line 34, the word "IN" should read "In"

In Column 17, line 7, the word "obseved" should read --observed--

In Column 19, line 2, delete the word "An" and replace it with the word "In"

In Column 19, line 4, delete the word "btween" and replace it with the word --between--

In Column 20, line 27, after the word "communication" insert the phrase -- with the--

In Column 20, line 28, after the word "said" delete the phrase --with the--

Signed and Sealed this

Twenty-fourth Day of August 1976

[SEAL]

Attest:

RUTH C. MASON
Attesting Officer

C. MARSHALL DANN
Commissioner of Patents and Trademarks